(12) United States Patent
Ryan

(10) Patent No.: US 10,786,664 B2
(45) Date of Patent: *Sep. 29, 2020

(54) NEEDLELESS, INTERMITTENT, NEUTRAL DISPLACEMENT IV INJECTION PORT

(71) Applicant: Fresenius Kabi Deutschland Gmbh, Bad Homburg (DE)

(72) Inventor: Dana Wm. Ryan, Nolensville, TN (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/003,162

(22) Filed: Jun. 8, 2018

(65) Prior Publication Data

US 2018/0289943 A1 Oct. 11, 2018

Related U.S. Application Data

(63) Continuation of application No. 14/939,835, filed on Nov. 12, 2015, now Pat. No. 10,105,529.

(Continued)

(51) Int. Cl.
*A61M 39/10* (2006.01)
*A61M 5/162* (2006.01)
*A61M 39/26* (2006.01)

(52) U.S. Cl.
CPC ......... *A61M 39/1011* (2013.01); *A61M 5/162* (2013.01); *A61M 2039/1072* (2013.01); *A61M 2039/262* (2013.01); *A61M 2039/267* (2013.01)

(58) Field of Classification Search
CPC ........ A61M 39/1011; A61M 2039/267; A61M 2039/262; A61M 5/162; A61M 2039/1072
See application file for complete search history.

(56) References Cited

U.S. PATENT DOCUMENTS

| 5,788,215 A | 8/1998 | Ryan |
| 5,833,213 A | 11/1998 | Ryan |

(Continued)

FOREIGN PATENT DOCUMENTS

| FR | 2910817 A1 | 7/2008 |
| JP | 2010012234 A | 1/2010 |

OTHER PUBLICATIONS

International Search Report arid Written Opinion from the International Searching Authority for International Application No. PCT/US2015/060363, dated Jan. 28, 2016 (12 Pages).

(Continued)

*Primary Examiner* — Amber R Stiles
(74) *Attorney, Agent, or Firm* — Cook Alex Ltd.

(57) ABSTRACT

An injection port assembly including a body having first and second mating structures configured to mate with a first connector for a first fluid pathway and a second connector on a device, respectively. A resilient barrier substantially contained within the body and compressible from a first position in which fluid flow between the first and second connectors is blocked to a more compressed second position in which fluid flow between the first and second connectors is permitted. A hollow cannula can be coupled with the first mating structure and disposed within the resilient barrier, the hollow cannula having a distal end configured to extend through the resilient barrier when the resilient barrier is in the second position, the distal end having lateral slots. The resilient barrier can have first and second annular sealing rings positioned above and below the lateral slots respectively.

9 Claims, 15 Drawing Sheets

Related U.S. Application Data

(60) Provisional application No. 62/078,740, filed on Nov. 12, 2014.

(56) References Cited

U.S. PATENT DOCUMENTS

| | | | | |
|---|---|---|---|---|
| 5,839,715 | A | * | 11/1998 | Leinsing ............... A61J 1/2096 251/149.1 |
| 5,954,313 | A | | 9/1999 | Ryan |
| 6,113,068 | A | | 9/2000 | Ryan |
| 6,299,131 | B1 | | 10/2001 | Ryan |
| 6,994,315 | B2 | | 2/2006 | Ryan et al. |
| 7,530,546 | B2 | | 5/2009 | Ryan et al. |
| 8,096,525 | B2 | | 1/2012 | Ryan |
| 2003/0050610 | A1 | * | 3/2003 | Newton ................ A61M 39/26 604/256 |
| 2007/0218757 | A1 | * | 9/2007 | Guala ................ A61M 39/045 439/589 |
| 2008/0249508 | A1 | * | 10/2008 | Lopez ................... A61M 39/10 604/533 |
| 2010/0030195 | A1 | | 2/2010 | Hishikawa et al. |
| 2010/0179514 | A1 | * | 7/2010 | Guala ................ A61M 39/045 604/537 |
| 2010/0249723 | A1 | | 9/2010 | Fangrow, Jr. |
| 2011/0024664 | A1 | * | 2/2011 | Burnard ............... F16K 15/147 251/324 |
| 2011/0282302 | A1 | * | 11/2011 | Lopez ................... A61M 39/10 604/247 |
| 2012/0109077 | A1 | | 5/2012 | Ryan |

OTHER PUBLICATIONS

Extended European Search Report from the European Patent Office for EP3218044, dated Aug. 7, 2018 (7 pages).

Translated Search Report by Registered Searching Authority Kosaido Co. Ltd. for corresponding Japanese Application No. JP2017536955, dated Sep. 11, 2018 (25 pages).

* cited by examiner

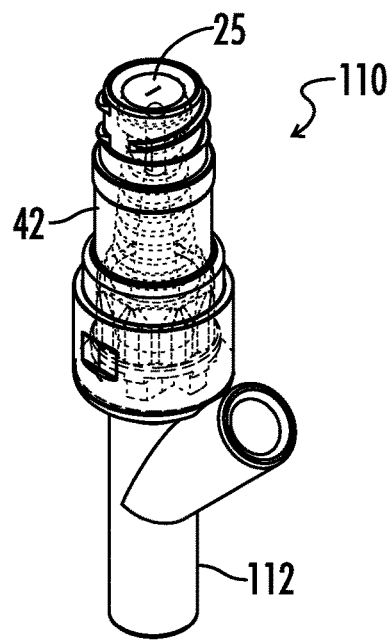
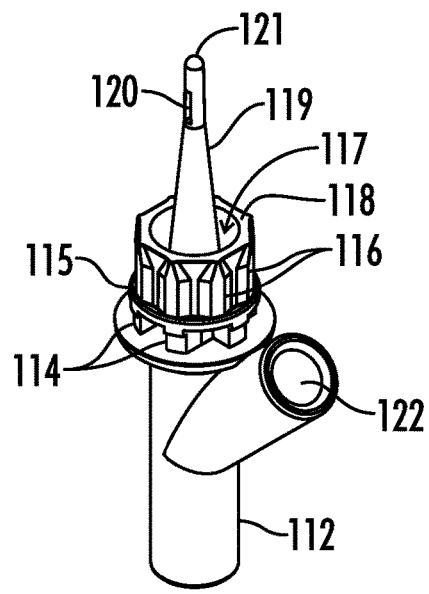
FIG. 9  FIG. 9a
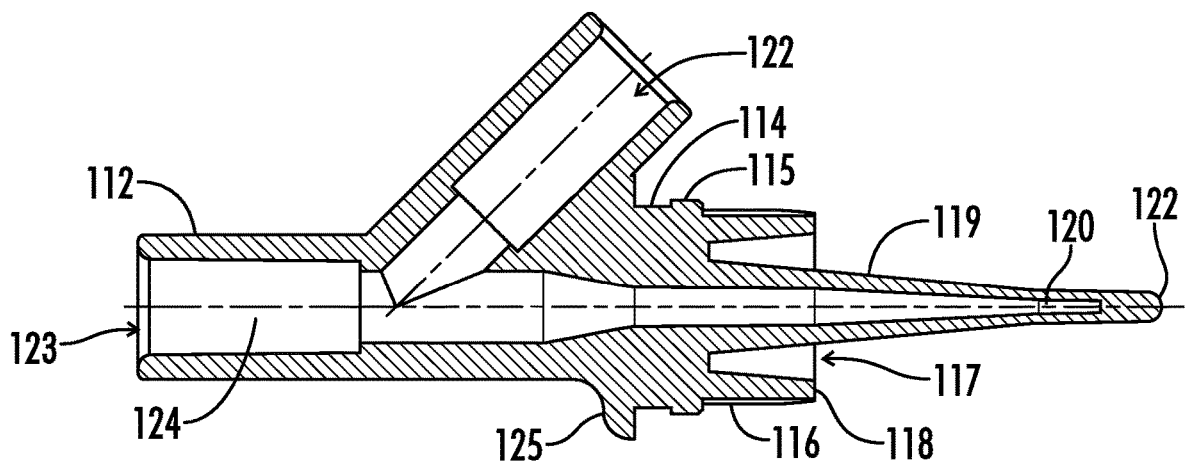
FIG. 9b

NEEDLELESS, INTERMITTENT, NEUTRAL DISPLACEMENT IV INJECTION PORT

CROSS-REFERENCE TO RELATED APPLICATIONS

This application claims the benefit of priority to U.S. Provisional Application No. 62/078,740, filed on Nov. 12, 2014, which is hereby incorporated by reference in its entirety. This application is also a continuation of U.S. patent application Ser. No. 14/939,835 filed on Nov. 12, 2015.

TECHNICAL FIELD OF THE INVENTION

The present disclosure relates generally to medical intravenous administration line connectors. More particularly, this disclosure pertains to a needleless, intermittent, neutral fluid displacement injection ports for safe infusion of IV fluids, antibiotics, lipids, blood, blood components or drug products and/or blood aspiration in intravenous and blood administration therapy.

BACKGROUND OF THE INVENTION

In the mid-1980's, concern grew publically worldwide within the healthcare community for a new and potentially lethal virus called the Human Immunodeficiency Virus (HIV) which leads to AIDS (Acquired Immune Deficiency Syndrome). Prior to the AIDS epidemic, IV therapy and blood collection methods utilized hypodermic syringes and IV sets utilizing steel needles and latex injection ports to administer drugs and IV fluids along with blood collection samples. An accidental needle stick injury among healthcare providers was a common occurrence. Various viruses, fungi and bacterial infections (i.e. Hepatitis A, B, and C, *Staphylococcus, Tuberculosis*) could be transmitted to the healthcare provider via an accidental needle stick injury. Accidental punctures by contaminated needles can inject hazardous fluids into the body through the skin. There is potential for injection of hazardous drugs, but contact with infectious fluids, especially blood, is by far the greatest concern. Even small amounts of infectious fluid can spread certain diseases effectively through an accidental needle stick injury. The AIDS epidemic was the catalyst for change from high risk steel needles to needleless injection port devices for intermittent intravenous therapy and/or blood collection within the healthcare community.

Conventional "standalone" needleless injection ports include a body having a first portion that can be mated at one end to any patient's vascular access catheter, IV extension set, Huber needle set or IV bags and a second portion that can be mated to a standard syringe (without a steel hypodermic needle) or IV administration set (without a steel hypodermic needle) in order to infuse IV fluids, drugs, antibiotics, blood products or other fluids through the injection port and into the patient's bloodstream. Conventional standalone needleless injection ports can also have a second portion that can be mated to a blood collection device or syringe in order to aspirate blood samples from the patient. These conventional needleless injection ports can also be incorporated into an IV pump set or IV administration set in a Y-Injection Port configuration. Among the early and conventional needleless injection port internal fluid path designs introduced into the market since the early 1990's, many had the sole purpose to prevent accidental needlestick injuries for the healthcare provider.

Over the past 25 years, various conventional needleless injection ports have been introduced that utilize different functional design methods incorporating a two-way (infusion and aspiration capabilities), valve-type system for intermittent fluid delivery or aspiration. A combination of a resilient barrier(s) or seal(s) (i.e. silicone), steel springs, steel needles, steel blunt needles, and thermoplastic components have been utilized in conventional needleless injection ports.

The patient could receive antibiotics, normal saline/heparin, and other drugs or fluids through a standard syringe, or IV therapy through an IV administration set/IV bag. Blood samples are generally taken through a standard syringe or a blood collection device for chemical analysis. As the various fluid delivery medical devices are coupled to the injection port, the male-luer component of each of these fluid delivery medical devices will push down on the resilient barrier or seal to open the fluid pathway of the injection port in order to infuse fluids or draw blood samples through the injection port. Once the infusion or aspiration procedure is completed, the syringe, IV administration set, or blood collection device is removed from the injection port, the internal valve system reseals with the intent to prevent contamination from entering into the injection port fluid pathway system and potential catheter-related bloodstream infections (CR-BSIs).

Ever since needleless, intermittent injection ports were introduced to the markets in the early 1990's, two major patient safety issues have evolved; a significant increase in catheter-related bloodstream infections (CR-BSIs) and intraluminal thrombotic catheter occlusions (blood clots within the vascular-access catheter). Prior to needleless injection ports being introduced to the market in the early 1990's, CR-BSI's or intraluminal thrombotic catheter occlusions were not reported in medical journals when utilizing steel hypodermic needles and latex injection ports. It appears that needleless injection ports solved one major healthcare issue of eliminating accidental needlestick injuries, but, inadvertently created new patient safety issues.

Intravascular catheters play a central role in the care of critically and chronically ill patients; an estimated 7 million central venous catheters (CVCs) and peripherally-inserted central catheters (PICCs) and over 300 million peripheral IV catheters (PIV's) are inserted in patients each year in the United States alone as an integral part of today's patient care paradigm. These devices allow the administration of, among other things, parenteral nutrition, antibiotics, pain medication and large fluid volumes as well as provide access for blood sampling and blood component delivery. However, more than 250,000 catheter-related bloodstream infections (CR-BSI's) have been reported in medical journals to occur annually, with an estimated mortality rate of 12% to 25% (30,000 to 60,000 CR-BSI associated deaths every year in the United States). CR-BSI is not only one of the highest mortality infections in the hospital, but it also significantly increases hospital length of stay, with additional health care cost estimates of over $50,000 per occurrence (over $12 billion annually).

A second patient safety issue that has developed since the introduction of needleless injection ports is intraluminal thrombotic catheter occlusions, or blood clots within the vascular-access catheter. Catheter occlusion is defined as a partial or complete obstruction of the catheter lumen that limits or prevents the ability to withdraw blood, flush the catheter, and/or administer parenteral solutions or medications. Characterized by the inability to withdraw blood or infuse liquids, catheter occlusions occur in up to 25% of all CVCs and PICCs and are associated with interrupted intravascular therapy, often requiring either pharmacologic or even surgical approaches to restore catheter patency. Any of these events can negatively affect the patient's hospital experience. Discomfort associated with catheter restarts and IV site manipulation directly impacts the patient's perception of quality of care. Clinical complications associated with catheter occlusions can cost significant time and money and are also a critical factor in the overall patient care equation. It has been reported in the literature that typically 190 CVC/PICC catheters become occluded due to intraluminal thrombosis for every 1,500 catheters placed. Inability to access the patient's vascular system is not the only negative side effect of thrombus formation and catheter occlusion. Defined as a positive blood culture with clinical or microbiological evidence strongly implicating the catheter as the source of infection, catheter-related bloodstream infections (CR-BSIs) have been shown to have a strong correlation with the presence of catheter thrombi and fibrin sheaths in both animal and human studies. It is surmised that an intraluminal thrombosis may serve as a nidus for infections, perhaps due to the blood fibrin and biofilm depositions, thereby affecting the patient's health and increasing hospital costs.

Conventional needleless injection ports may also have other functional design deficiencies that could contribute to the increase in the two critical catheter care and maintenance issues facing healthcare today; catheter-related bloodstream infections (CR-BSIs) and intraluminal thrombotic catheter occlusions.

Poorly designed septum seal integrity, large gaps or openings at the critical outer septum area (or entry point), could allow microbial contamination ingress into the patient's injection port fluid pathway. Additionally, septum surface designs could make effective disinfection of the septum surface very difficult prior to accessing the needleless injection port; which could lead to downstream contamination into the patient's bloodstream. Most conventional needleless injection ports have torturous fluid pathways within their valve system designs that exhibit dead spaces that are difficult to effectively flush blood, air bubbles, and/or critical drugs from the injection port. Entrapped blood, within 24 hours, could begin developing blood fibrin and biofilm colonies within the injection port itself. The blood fibrin buildup within the injection port fluid pathway dead spaces can become a food source for microorganisms. Many conventional needleless injection ports with torturous fluid pathway valve designs have multiple-moving valve components within the fluid pathway of the injection port. This leads to large priming volumes (the amount of fluid to fill the fluid pathway of the needleless injection port), which increases the possibility for dead spaces within the injection port fluid pathway. Also, the majority of conventional needleless injection ports on the market exhibit either a negative or positive fluid displacement functional feature that exhibits a reflux of the patient's blood into the catheter lumen immediately upon disconnecting a syringe or IV set from the injection port (Negative Fluid Displacement designs) or reflux of the patient's blood immediately upon connecting a syringe or IV set to the injection port (Positive-Pressure Displacement designs). Most needleless injection ports are accessed many times over the life of the product; typically the life cycle for a conventional injection port is up to 72 to 96 hours before being replaced in an acute care hospital, and up to 7 days in a home care setting. This is due to a concern for potential infection and/or occlusion occurring. Each time blood is refluxed into the catheter lumen, blood fibrin develops on the inner wall of the catheter. The blood fibrin buildup contributes to intraluminal thrombotic catheter occlusions and becomes the food source for microorganisms coming down from the needleless injection port. The problems mentioned above can potentially be harmful to a patient or otherwise undesirably jeopardize the safety of the patient.

Additionally, the first and second portions of the injection port body in many conventional needleless injection ports are either sonically-welded or solvent-bonded together during the assembly process in manufacturing in order to firmly connect the two portions together and create an internal seal within the body. This manufacturing process can be difficult and time consuming, as well as costly.

What is needed, then, are improvements to a new needleless, intermittent injection port that is designed to reduce catheter-related bloodstream infections (CR-BSIs) and intraluminal thrombotic catheter occlusions, thereby, improving better patient safety and care.

BRIEF SUMMARY OF THE INVENTION

One aspect of the present disclosure is a needleless, intermittent, injection port assembly for coupling to and uncoupling from a first fluid pathway of a first connector and for coupling to a fluid delivery medical device provided with a second connector so as to provide fluid connection between the first and second connectors. The injection port assembly can include a body having a first mating structure configured to mate with the first connector and a second mating structure coupled to the first mating structure and configured to mate with the second connector. A resilient microbial barrier substantially contained within the body can be compressible from a less compressed first position in which fluid flow between the first connector and the second connector is blocked to a more compressed second position in which fluid flow between the first connector and the second connector is permitted.

In some embodiments, the injection port assembly can include a hollow cannula coupled with the first mating structure and disposed within the resilient microbial barrier. The hollow cannula can have a distal end configured to extend through the resilient microbial barrier when the resilient microbial barrier is in the more compressed second position. The distal end can have a lateral fluid pathway slots. The resilient microbial barrier can include an upper annular sealing ring positioned above the lateral fluid pathway slots, and a second annular sealing ring positioned below the lateral fluid pathway slots. As such, the annular sealing rings can help form a first seal above the lateral slots to improve fluid leakage and back pressure capabilities, and a second seal below the lateral slots, which can help prevent fluid leakage between the hollow cannula and internal wall of the resilient microbial barrier.

In some embodiments, the injection port assembly can include a first locking portion disposed on the first mating structure and a second locking portion disposed on the second mating structure. The second locking portion can correspond to the first locking portion such that the first and second locking portions are configured to lock together to couple the first mating structure to the second mating structure. In one embodiment, the first locking portion can be a protrusion or snap lock ring extending from the first mating structure, and the second locking portion can be a snap lock channel defined in the second mating structure, the snap lock channel configured to receive the protrusion or snap lock ring to secure the first and second mating structures together.

In another embodiment, the second mating structure can have a distal end extending away from the first mating structure. The second mating structure distal end can include a flange extending laterally inward, the flange including an inner tapered sealing surface and a lower sealing surface positioned below the inner tapered surface. The resilient barrier can include an upper sealing surface and a second sealing surface. The inner tapered surface and the lower sealing surface of the second mating structure can be configured to sealingly compress upper sealing surface and second sealing surface of the resilient barrier respectively. In some embodiments, the inner tapered surface of the second mating structure can define an opening having an opening diameter. The resilient barrier can have a resilient barrier distal end having an uncompressed barrier distal end diameter, the resilient barrier distal end positioned within the opening when the resilient barrier is in the less compressed first position. The ratio of the uncompressed barrier distal end diameter to the opening diameter can be greater than about one, such that as the resilient microbial barrier moves to the less compressed first position, the distal end of the resilient microbial barrier meets the inner tapered sealing surface of the flange, and the flange applies an inward compression force on the distal end of the resilient barrier. The resilient barrier can include a lower sealing flange that can be sealingly compressed between the first and second mating structures when the first and second mating structures are coupled together.

One objective of the present disclosure is to provide an improved compression-fit septum seal integrity with reduced gaps or openings, and improved septum disinfection capabilities with a 3-piece component assembly.

Another objective of the present disclosure is to provide a needleless, intermittent, injection port that is latex-free, non-DEHP, and Bisphenol-A free.

Another objective of the present disclosure is to allow both male-luer lock and male-luer slip medical device fluid delivery connectors to be compatible with an needleless, intermittent injection port for infusion of all fluids and aspiration of blood products.

Another objective of the present disclosure is to provide a needleless, intermittent, injection port assembly with a substantially neutral fluid displacement feature.

Another objective of the present disclosure is to provide a needleless, intermittent, injection port assembly with a straight-through, reverse-split septum hollow fluid pathway cannula design with one or more lateral fluid path ports.

Another objective of the present disclosure is to provide an improved, non-torturous, fluid pathway with reduced dead space, small priming volume, clinically acceptable fluid flow rates for all medical procedures, and excellent blood flushing characteristics.

Another objective of the present disclosure is to prevent fluid leakage within the injection ports fluid pathway, and improve back-pressure capabilities.

Another objective of the present disclosure is to help eliminate the use of hypodermic needles with the needleless, intermittent, injection port. The invention will not need hypodermic needles to be used, thereby complying with United States Federal, State and OSHA laws and mandates under the various safety needle laws.

Another objective of the present disclosure is to help provide an improved manufacturing assembly process to help reduce overall costs and to help increase productivity for the final assembly of the injection port.

Numerous other objects, advantages and features of the present disclosure will be readily apparent to those of skill in the art upon a review of the following drawings and description of a preferred embodiment.

BRIEF DESCRIPTION OF THE SEVERAL VIEWS OF THE DRAWINGS

FIG. 9 is a perspective view of another embodiment of a needleless, intermittent, injection port assembly having a Y-site configuration.

FIG. 9a is a perspective view of a first mating structure of the Y-site injection port assembly of FIG. 9.

FIG. 9b is a cross-sectional view of the first mating structure of FIG. 9a.

DETAILED DESCRIPTION

Figure 1:
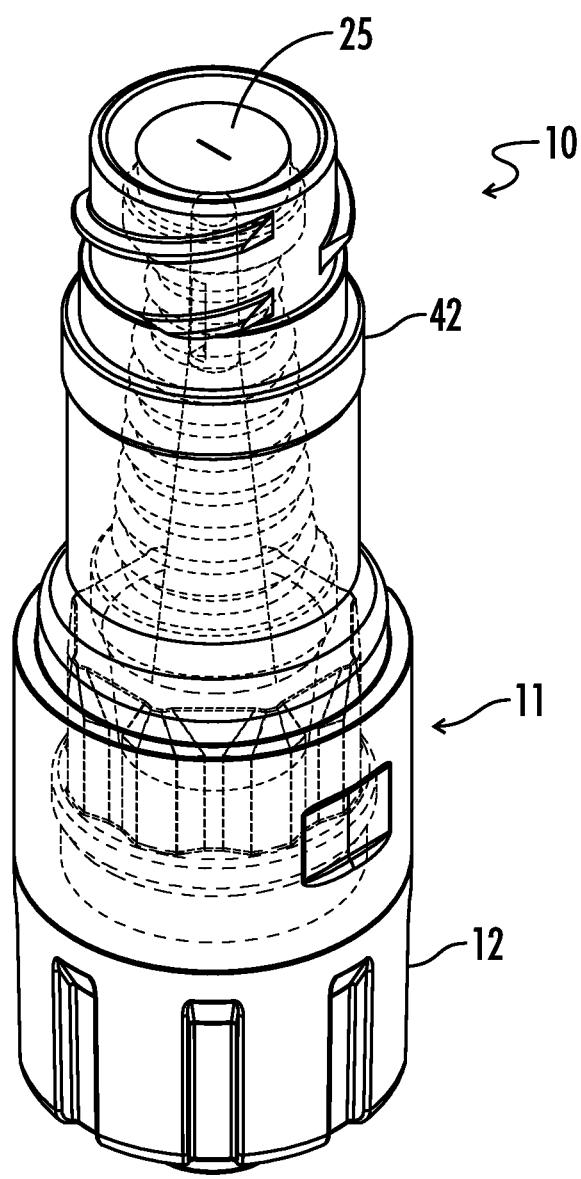
FIG. 1 is a perspective view of an embodiment of a "standalone," needleless, intermittent, substantially neutral displacement injection port assembly.

While the making and using of various embodiments of the present invention are discussed in detail below, it should be appreciated that the present invention provides many applicable inventive concepts that is embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

As described herein, an upright position is considered to be the position of apparatus components while in proper operation or in a natural resting position as described herein. Vertical, horizontal, above, below, side, top, bottom and other orientation terms are described with respect to this upright position during operation unless otherwise specified. The term "when" is used to specify orientation for relative positions of components, not as a temporal limitation of the claims or apparatus described and claimed herein unless otherwise specified. The term "lateral" denotes a side to side direction when facing the "front" of an object.

The phrase "in one embodiment," as used herein does not necessarily refer to the same embodiment, although it may. Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the apparatuses and/or methods disclosed and claimed herein may be made and/or executed without undue experimentation in light of the present disclosure. While the apparatuses and methods of this invention have been described in terms of the embodiments included herein, it will be apparent to those of ordinary skill in the art that variations may be applied to the apparatuses and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Figure 7:
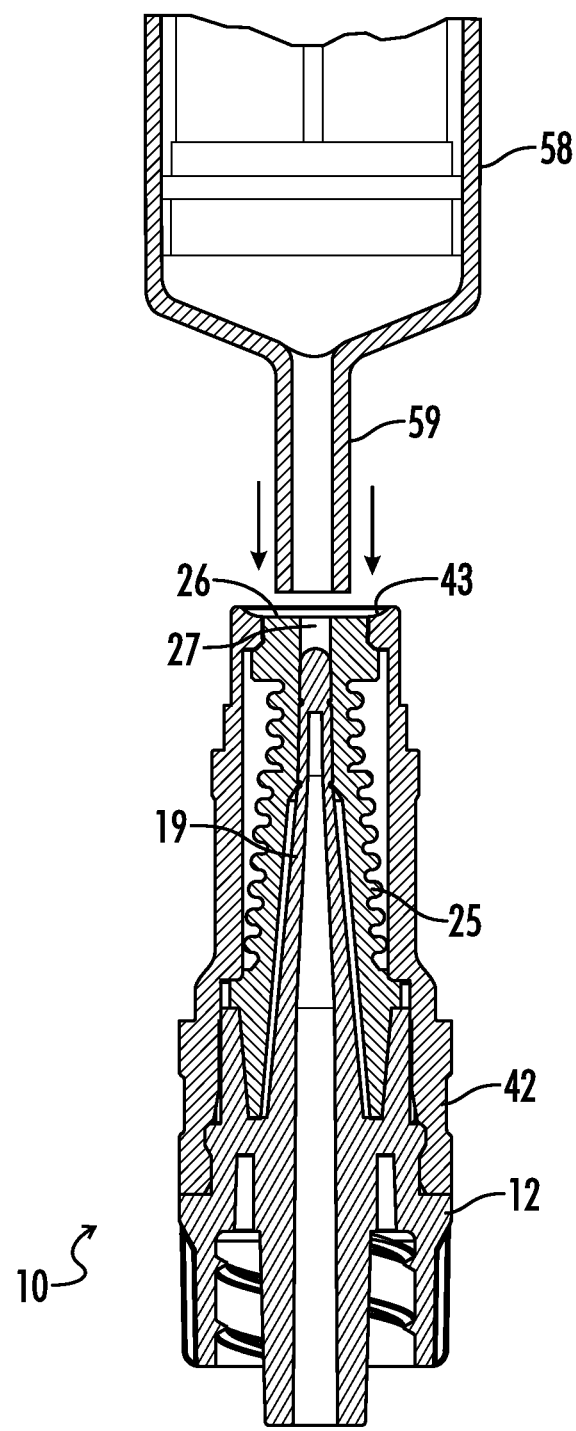
FIG. 7 is a cross-sectional view of a second connector male-luer slip syringe moving forward to couple with the "standalone" needleless, intermittent, injection port assembly of FIG. 1.
Figure 8:
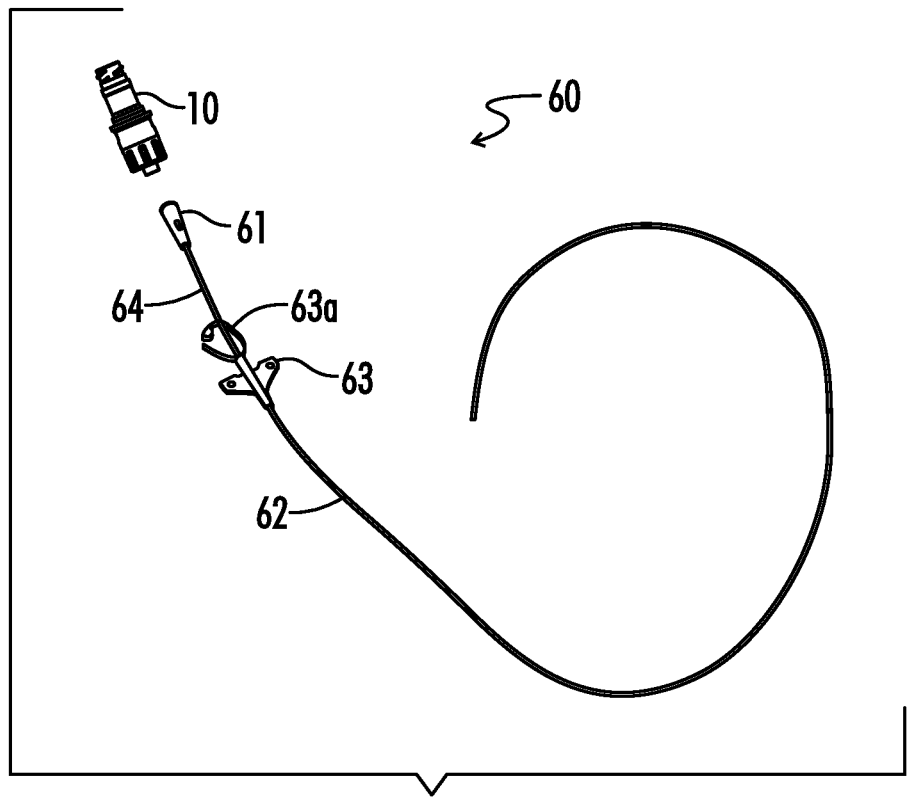
FIG. 8 is a perspective view of the "standalone" needleless, intermittent, injection port assembly of FIG. 1 being coupled to a first connector; a single-lumen peripherally-inserted central catheter (PICC).
Figure 8A:
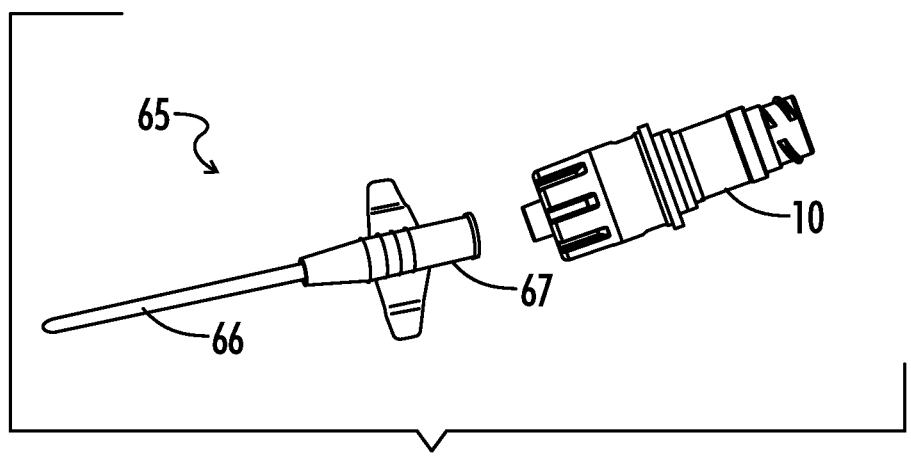
FIG. 8a is a perspective view of the "standalone" needleless, intermittent, injection port assembly of FIG. 1 being coupled to another type of first connector; a short-term, peripheral IV catheter (PIV).
Figure 8B:
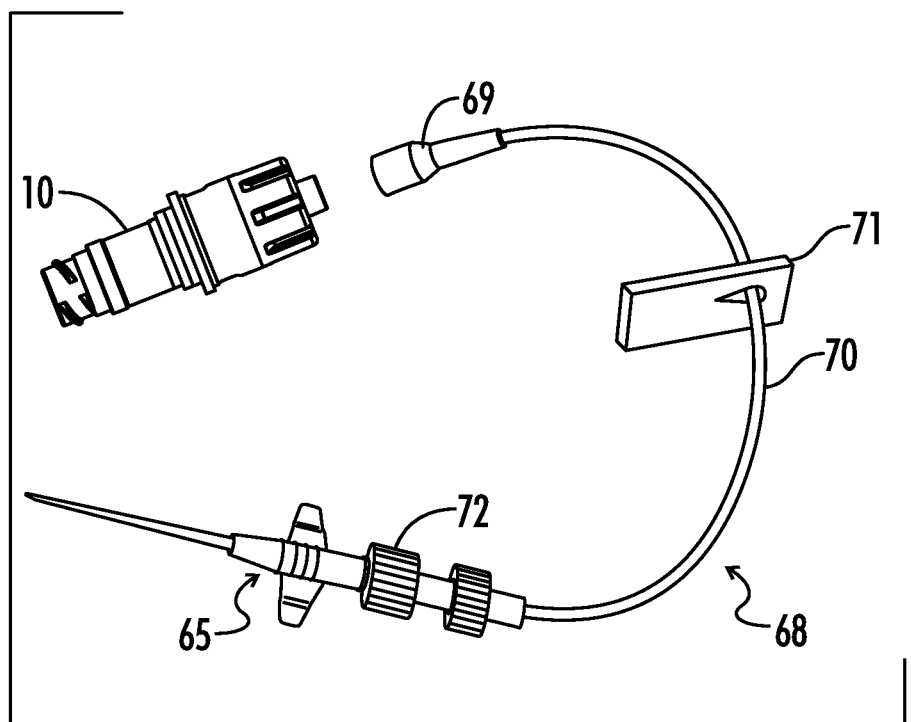
FIG. 8b is a perspective view of the "standalone" needleless, intermittent, injection port assembly of FIG. 1 being coupled to another type of first connector; a single-lumen catheter extension set.
Figure 10:
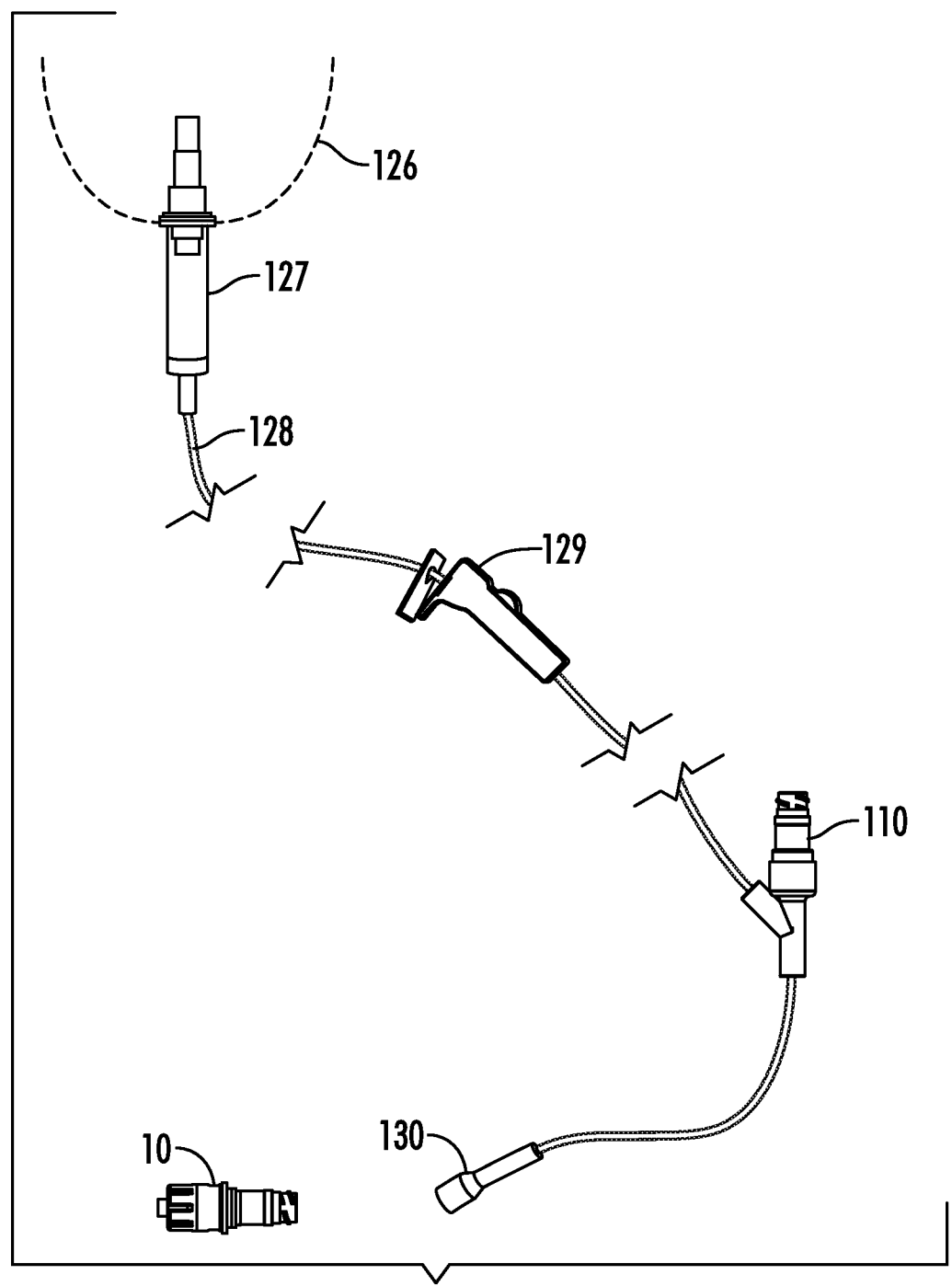
FIG. 10 is a perspective view of the needleless, intermittent, Y-site injection port assembly of FIG. 9 incorporated into a typical gravity-fed IV administration set.

FIG. 1 is an embodiment of a "standalone", needleless, intermittent intravenous injection port assembly 10. The assembly 10 can include a body 11. The body 11 can include a first mating structure 12 and a second mating structure 42. The injection port assembly 10 can be used for coupling to and uncoupling from a first fluid delivery pathway of a first connector such as a vascular-access central venous catheter as shown in FIG. 8, to a peripheral IV catheter (PIV) as shown in FIG. 8a, or to an catheter extension set as shown in FIG. 8b. The above vascular-access catheters shown in FIGS. 8 and 8a are inserted into a patient's venous circulatory system. The needleless injection port; once coupled to the venous-access catheter, allows for intermittent IV therapy and infusion of pain management medications, parenteral nutrition, antibiotics, lipids, large fluid volume therapy, blood and blood products, anesthetic medications, or blood collection. The vascular-access catheters and the catheter extension set could have one or more female lumens to which the assembly 10 can be coupled. The injection port assembly 10 can also be used for coupling to and uncoupling from a second connector such as a standard syringe (with no hypodermic needle) as shown in FIG. 7, an IV administration set male-luer connector as shown in FIG. 10, a blood collection tube holder, or various other connectors which can be used to infuse or collect medication, fluids, or blood from a patient.

Referring again to FIG. 1, the injection port assembly 10 can also include a resilient microbial barrier 25 substantially contained within the body 11 and compressible from a less compressed first position to a more compressed second position. Once the second connector fluid delivery medical devices are coupled to the second mating structure 42, the second connectors can further compress the resilient microbial barrier 25, exposing the lateral fluid pathway slots 20 of the hollow cannula 19, shown in FIG. 3, allowing for infusion of fluids to the patient or aspiration of blood from the patient by means of a standard syringe or blood collection tube holder and blood collection vacuum tubes. It will be readily apparent to those of skill in the art upon a review of the following figures that syringes, catheter extension sets, IV administration sets, and blood tube collection holders male-luer connections can be either have a male-luer slip or a male-luer lock configuration.

Figure 2:
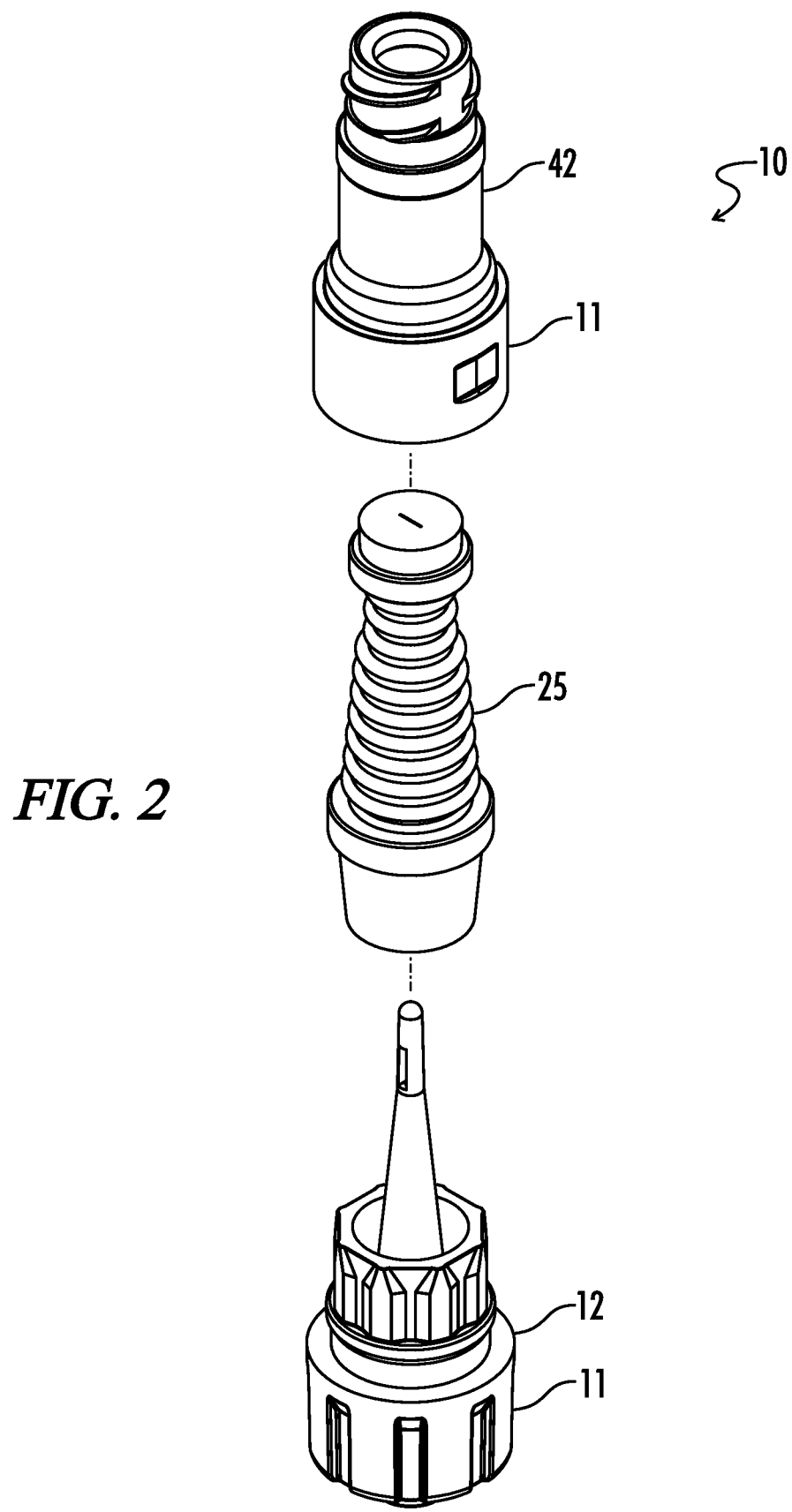
FIG. 2 is an exploded perspective view of the "standalone" needleless, intermittent, injection port assembly of FIG. 1.

In FIG. 2 depicts an exploded perspective view of the "standalone" needleless, injection port assembly 10 of FIG. 1. It shows the first mating structure 12, the resilient microbial barrier 25, and the second mating structure 42 being assembles. The resilient microbial barrier 25 can be positioned between the first and second mating structures 12 and 42 such that when the first and second mating structures 12 and 42 are coupled together, the microbial barrier 25 can be substantially contained within the body 11 of the injection port assembly 10.

Figure 3:
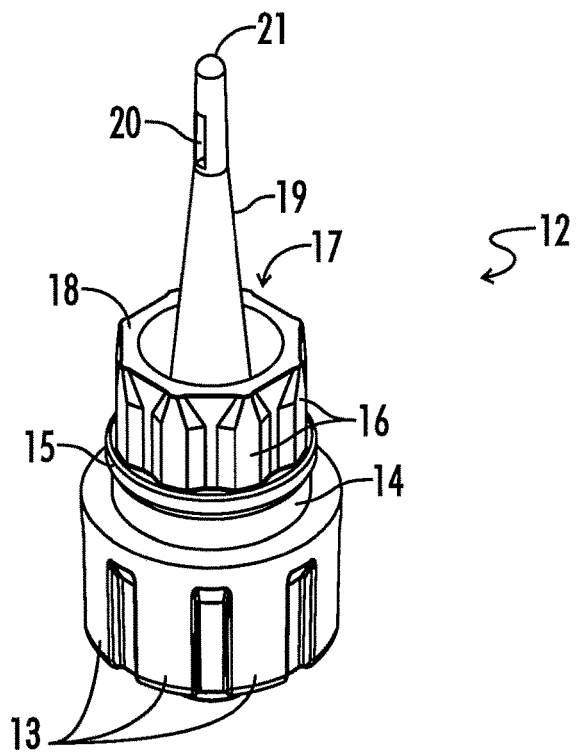
FIG. 3 is a perspective view of an embodiment of a first mating structure from the "standalone" needleless, intermittent injection port assembly of FIG. 2.

In FIG. 3, a perspective view of the first mating structure 12 of the injection port assembly of FIG. 1 is shown. The selected plastic material for the first mating structure 12 will be latex-free, non-DEHP, and Bisphenol-A free for improved patient safety. The proximal finger grips 13 can be located on an external surface of the first mating structure 12 and can help assist the healthcare provider when coupling the injection port assembly to the first connector system as described in FIG. 1. The stabilizing ring shelf 14 is designed to stabilize the second mating structure 42 on the first mating structure via stabilizing ring securement segments 57, shown in FIG. 5a. A snap-lock ring feature 15 securely; by mechanical press-fitting, couples the first mating structure 12 to the second mating structure 42 during assembly, by coupling the snap-lock ring 15 to the second mating structure snap-lock ring channel 56, as shown in FIG. 6. A first series of anti-rotation and self-guiding ratchets 16, shown in FIG. 3, are designed to couple with a second set of anti-rotation and self-guiding ratchets 55 of the second mating structure 42, shown in FIG. 5a. The self-guiding ratchets can allow for full assembly automation of the body 11 without the need for indexing the components. Referring again to FIG. 3, the sealing ring shelf 18 is the base on which the resilient microbial barrier 25 lower flange ring 32, shown in FIG. 4, sits on for a compression-fit sealing surface after assembly. Referring again to FIG. 3, a sealing well 17 is designed to couple with the resilient microbial barrier 25 lower compression-fit well ring 35, shown in FIG. 4, to form an additional fluid seal after assembly.

Figure 3A:
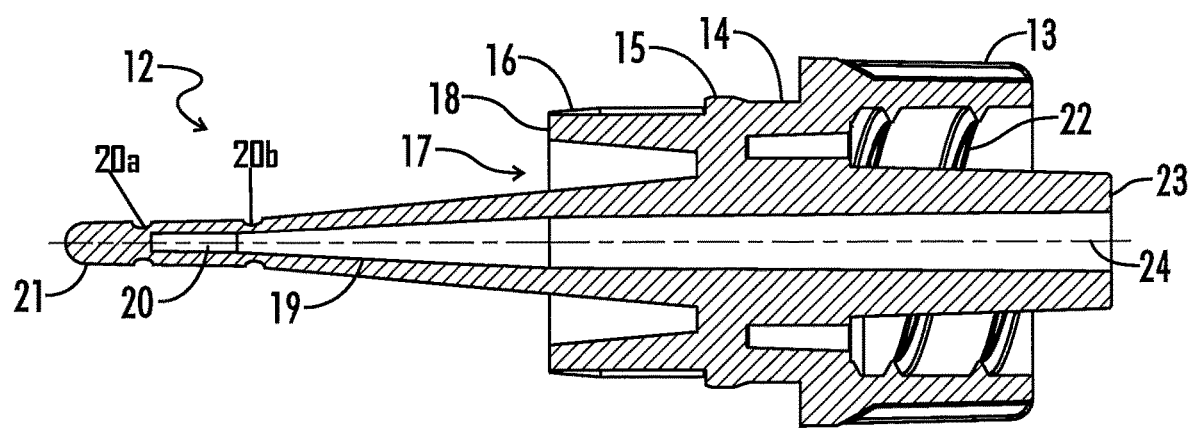
FIG. 3a is a cross-sectional view of the first mating structure of FIG. 3.

Referring to FIG. 3a, which is a cross-sectional view of the first mating structure 12 of FIG. 3, a hollow fluid pathway cannula 19 can be integrally formed with the first mating structure 12. The fluid pathway 24 can be a straight-through and non-tortuous pathway to help reduce or eliminate any dead space within the fluid pathway 24 which can help minimize any blood fibrin or biofilm adhesion, development, and colonization. Additionally, a non-torturous fluid pathway can help provide a small priming volume, and help provide clinically-acceptable fluid flow rates. Along the upper portion of the hollow cannula 19 are lateral fluid pathway holes or slots 20. A first annular groove 20a is positioned proximally from the slots 20, and a second annular groove 20b is spaced distally from the slots 20. On the distal end of the hollow cannula 19 is a full radius bullet-nose feature 21. This type of distal end is designed to increase the number of coupling and uncoupling events over the life-cycle of the injection port.

A first set of threads 22 and male luer tip 23 can be used to securely couple and seal against fluid leakage with a first connector system (i.e. vascular-access catheters). In some embodiments, the first set of threads 22 can be a standard ISO 594 thread type. The hollow cannula 19 is shown to be an integral part of the first mating structure 12. The straight-through, non-tortuous, fluid pathway 24 is shown within the hollow cannula 19. The upper distal end lateral side fluid pathway holes or slots 20 of the hollow cannula 19 are shown along with the distal end bullet-nose feature 21.

Figure 4:
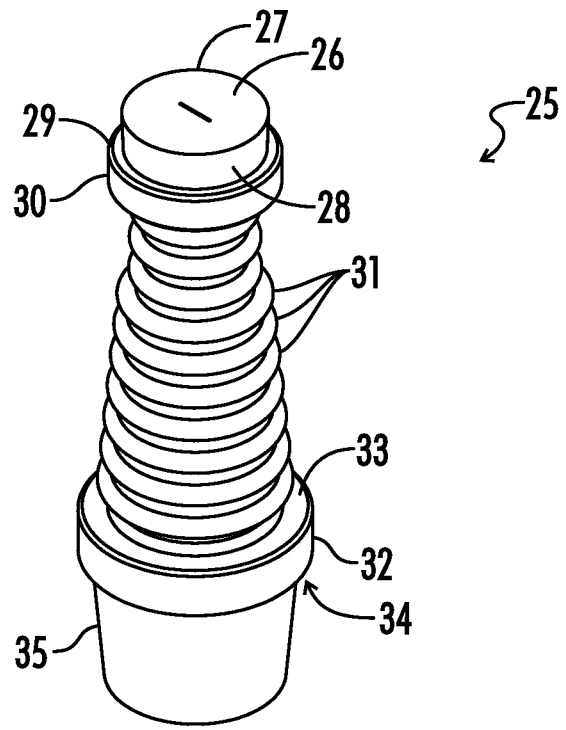
FIG. 4 is a perspective view of an embodiment of a resilient microbial barrier from the "standalone" needleless, intermittent, injection port assembly of FIG. 2.

FIG. 4 is a perspective view of the resilient microbial barrier 25 of the injection port assembly 10 in FIG. 1. The resilient microbial barrier 25 can include a flat septum surface 26 with a post-operation razor pre-slit 27. The septum surface 26 is flat and smooth to improve the ability to effectively disinfect the septum surface 26 of microorganisms prior to coupling of a fluid delivery medical device (i.e. syringe, IV administration sets, blood collection devices). An effective disinfection of the septum surface 26 can help protect the patient from potential downstream contamination. The septum 26 can be the first line of defense from contamination. The upper sealing surface 28 can form a compression-fit with the male-luer taper circular wall 45 of the second mating structure 42 shown in FIG. 5a after assembly when the microbial barrier 25 is in the less compressed first position. This compression-fit feature can help eliminate any gaps or potential leakage openings between the septum 26 and the male-luer taper circular wall 45 thereby minimizing any contaminated gross particulate matter from entering into an interior space 52 of the second mating structure 42. If contaminated gross particular matter does penetrate into the interior space 52, it is outside the patient's fluid pathway and would be extremely difficult to penetrate the resilient microbial barrier and enter into the lateral side fluid pathway holes or slots of the hollow cannula. Referring again to FIG. 4, a lower sealing surface 29 on resilient microbial barrier 25 can mate with a secondary sealing ring or surface 51 on the second mating structure 42, shown in FIG. 5a after assembly when the resilient microbial barrier is in the less compressed first position.

Figure 4A:
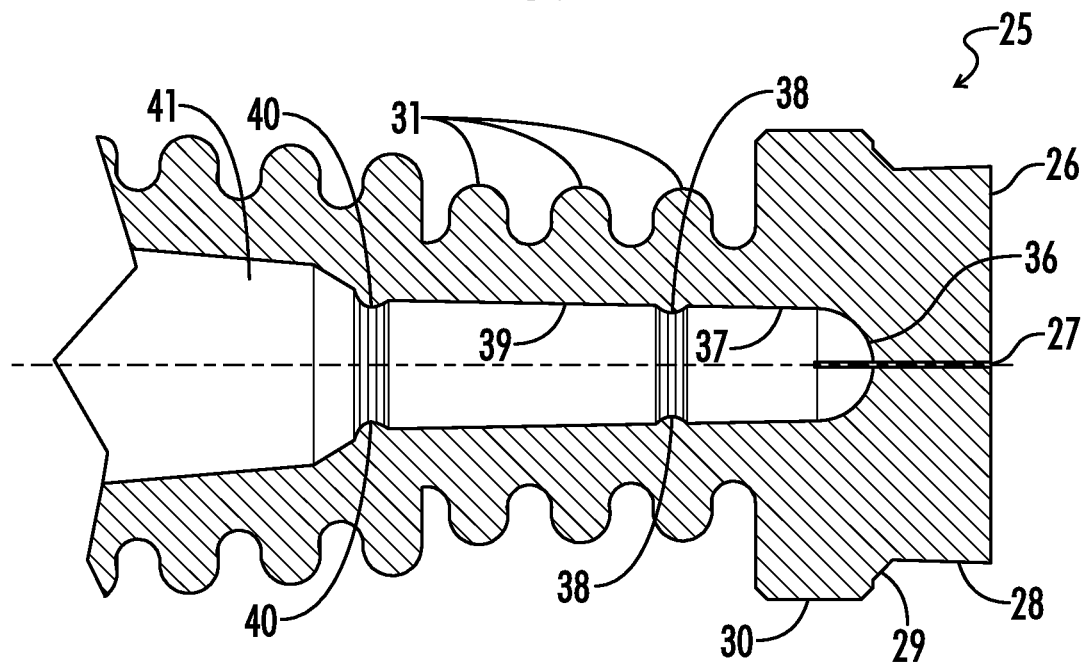
FIG. 4a is a partial cross-sectional view of an upper portion of the resilient microbial barrier of FIG. 4.
Figure 6:
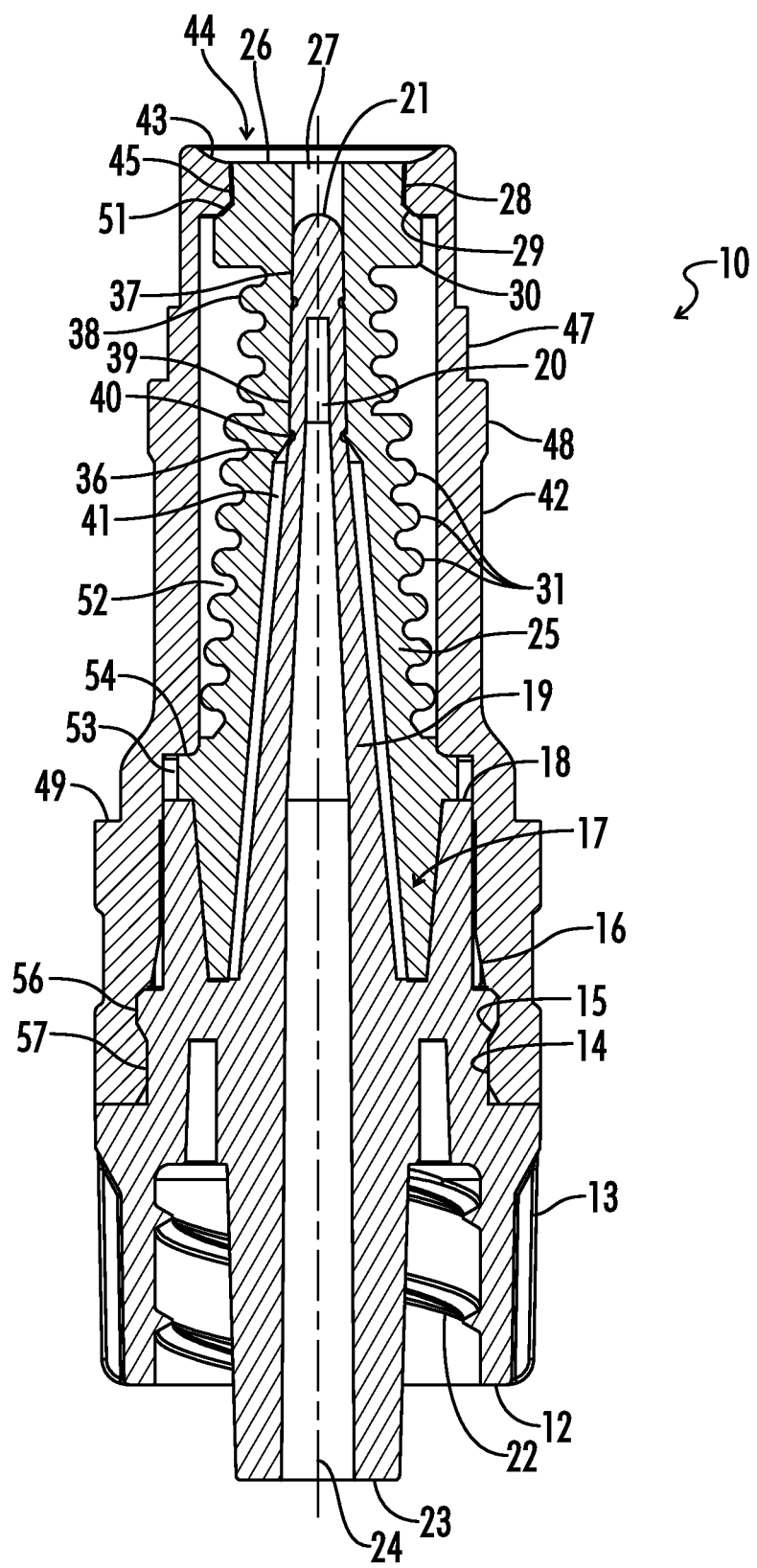
FIG. 6 is a cross-sectional view of the "standalone" injection port assembly of FIG. 1.
Figure 6A:
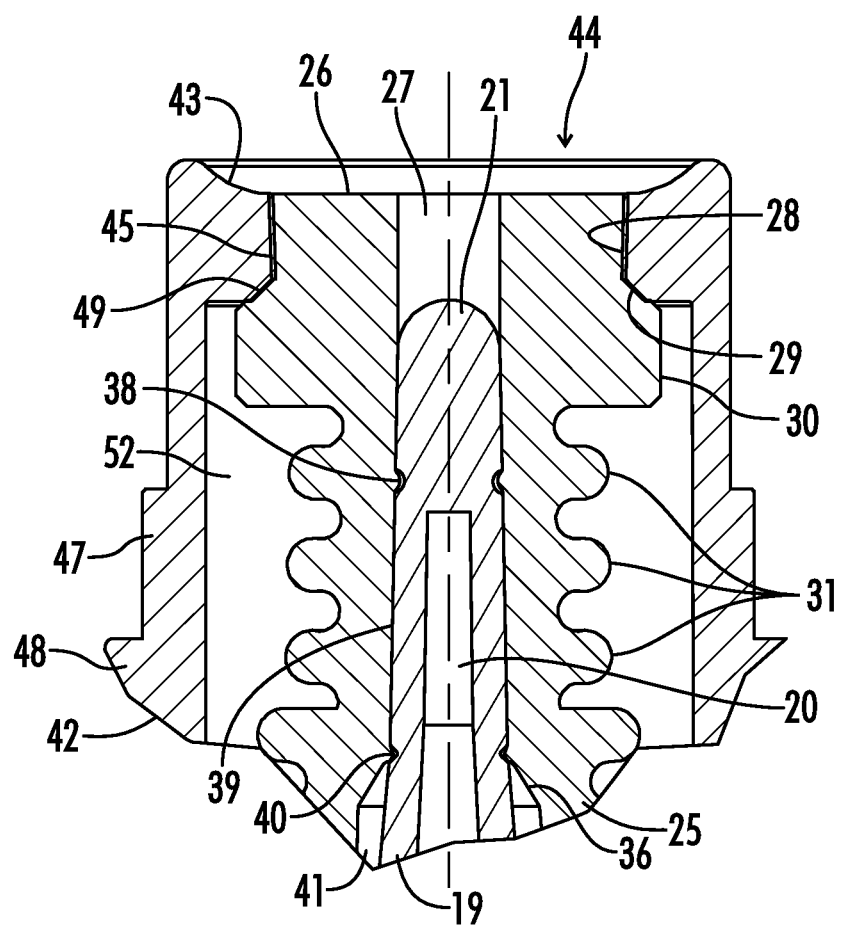
FIG. 6a is a detailed cross-sectional view of an upper portion of the injection port assembly of FIG. 6.

The upper sealing surface 28 and the lower sealing surface 29 of the resilient microbial barrier 25 can alternatively be referred to as first and second sealing surfaces 28 and 29. As best seen in FIG. 4a, the first sealing surface 28 intersects the second sealing surface 29. The male luer taper circular wall 45 and the secondary sealing surface 51 of the second mating structure 42 can alternatively be referred to as a first inner tapered body surface 45 and a second inner tapered body surface 51 of the second mating structure 42. As best seen in FIG. 6a, the first inner tapered body surface 45 narrows in the proximal direction and the second inner tapered body surface 51 widens in the proximal direction. When the resilient microbial barrier 25 is in the less compressed first position as illustrated in FIGS. 6 and 6a the first sealing surface 28 sealingly engages the first inner tapered body surface 45 and the second sealing surface 29 sealingly engages the second inner tapered body surface 51.

Referring again to FIG. 4, the lower sealing surface 29 can additionally help prevent contaminated gross particulate matter from entering into the interior space 52 of the injection port. The resilient microbial barrier 25 can include an upper centering circular flange 30 which can help keep the resilient microbial barrier 25 centered within the second mating structure and centered on the hollow cannula during coupling to and uncoupling from the second mating structure. A series of spring-like accordion flutes 31 are designed to fully encompass the hollow cannula. As a second connector is coupled to the injection port assembly and the resilient barrier 25 moves from the less compressed first position to the more compressed second position, the accordion flutes 31 can become more compressed. Upon removal of the second connector, the stored spring energy in the accordion flutes 31 can cause the resilient barrier 25 to return to the less compressed first position. The resilient microbial barrier 25 can be dimensioned such that when the first and second mating structures are coupled together, and the resilient microbial barrier 25 is positioned within the body, the resilient microbial barrier can be longitudinally compressed a predetermined distance such that after assembly, the resilient microbial barrier 25 in the first position is in a less compressed, or semi-compressed state. In some embodiments, the resilient microbial barrier 25 can be compressed by a distance of 0.050 inches when the resilient microbial barrier 25 is in the less compressed first position. This semi-compressed state pushes the distal circular septum 26 and the first and second circular sealing surfaces 28 and 29 into a mechanical compression-fit against the corresponding male-luer tapered wall and the secondary circular sealing surface of the second mating structure respectively. These compression-fit seals can help reduce contaminated gross particulate-matter from entering into the interior space of the injection port, improve the effectiveness of septum surface 26 disinfection with a healthcare facility approved disinfectant prior to coupling to the second connector, and reduce the possibility of a catheter-related bloodstream infection for the patient.

The lower circular sealing flange 32 can be configured to rest or mate on the sealing shelf of the first mating structure. When the injection port assembly is assembled, the lower circular sealing flange 32 can substantially fill the resilient microbial barrier lower flange space 53, as shown in FIG. 6. The lower flange 32 has two sealing surfaces, a lower flange upper sealing surface 33 and a lower flange lower sealing surface 34. The lower flange lower sealing surface 34 sits on the sealing shelf 18 of the sealing well 17. The lower flange upper sealing surface 33 can be compressed by a lower sealing ring surface 54 of the second mating structure 42 after the assembly of the first and second mating structures 12 and 42. In some embodiments, lower flange upper sealing surface can be compressed by a distance of approximately 0.060 inches. A compression fit seal can be formed between the lower flange lower sealing surface 34 and the sealing shelf 18 and another compression fit seal can be formed between the lower flange upper sealing surface 33 and the lower sealing ring surface 54 of the second mating structure 42. These compression-fit seals are designed to hermetically-seal the injection port interior spaces 52 and 41 from fluid and air leakage, which could allow microorganisms to enter into the injection port 10, or leak potentially caustic chemotherapy or other similar fluids from the injection port 10. The resilient microbial barrier 25 can include a tapered well ring 35 which can be configured to substantially fill the tapered well 17 of the first mating structure 12. An outer diameter of the well ring 35 can be slightly larger than an outer diameter of the diameters of the well 17 of the first mating structure, such that another mechanical, compression-fit seal can be formed between an outer wall of the well ring 35 and an outer wall of the well 17. The seal between the outer walls of the well ring 35 and the well 17 can provide an additional layer of protection from contaminants or fluids from entering or exiting the interior space 41 between the cannula 19 and the resilient barrier 25.

FIG. 4a is a partial cross-sectional view of an upper portion of the resilient microbial barrier 25 in FIG. 4. The upper distal interior wall of the barrier 25 can include two annular sealing rings, an upper sealing ring 38 and a lower sealing ring 40. Those of ordinary skill in the art will recognize that the interior wall of the barrier 25 could have two or more annular sealing rings to offer additional sealing surfaces. The upper, annular sealing ring 38 has a diameter slightly smaller than the outer diameter of the hollow cannula, and can be positioned above the side fluid pathway slots on the hollow cannula when the resilient microbial barrier 25 is in the first position. Thus, when the resilient microbial barrier 25 is in the first position, the upper annular sealing ring 38 can be compressed, and a mechanical compression fit seal can be formed between the upper annular sealing ring 38 and the cannula 19. This mechanical compression-fit seal can help improve fluid back pressure capabilities and minimize fluid leakage through from the side fluid pathway slots and the fluid pathway out of the razor slit 27 and the septum surface 26 of fluids. Thus, upper annular sealing ring 38 can help prevent caustic chemotherapy fluids or other harmful chemicals from leaking out of the injection port assembly 10. The lower, annular sealing ring 40 also has a diameter slightly smaller than the outer diameter of the hollow cannula, and is located below the side fluid pathway slots on the hollow cannula when the resilient microbial barrier 25 is in the less compressed first position. As such, another mechanical compression fit seal can be formed between the resilient barrier 25 and the cannula below the side fluid pathway slots. This mechanical compression-fit seal can help minimize any fluid leakage below the lower annular sealing ring 40 into the space 41 between the lower wall of the resilient microbial barrier 25 and the outer wall of the hollow cannula, thereby, minimizing the possibility of contamination within this space. The annular sealing rings 38 and 40 may be received in the circular grooves 20a and 20b, respectively, in the hollow cannula 19 when the microbial seal 25 is in the less compressed first position, as shown in FIG. 6, to more positively seat the sealing rings with respect to the fluid pathway slots. An interior wall surface 39 can be located between the two annular sealing rings 38 and 40. The diameter of the interior wall surface 39 in some embodiments can be substantially equal to the diameter of the cannula 19 and the bullet tip nose 21. Additionally, resilient microbial barrier can include a bullet nose mating surface 36 having a shape complimentary to the shape of the bullet nose of the hollow cannula. As such, the amount of dead space between the resilient microbial barrier 25 and the cannula 19 can be significantly reduced when the resilient barrier 25 is in the less compressed first position. Such an embodiment can help reduce the potential for back flow pressure within the fluid pathway, which can help prevent intraluminal thrombotic catheter occlusions from forming within the fluid pathway. The above compression-fit annular sealing rings and the diameter matches described above can help reduce dead space within the fluid pathway and produce a substantially neutral fluid displacement (virtually no blood reflux at the tip of a vascular-access catheter) within the fluid pathway. A reduction of blood reflux into the lumen of the vascular-access catheter immediately upon coupling to the injection port or immediately upon uncoupling a second connector from the injection port can help reduce the number of intraluminal thrombotic catheter occlusions (blood clots within the vascular-access catheter lumen) and catheter-related bloodstream infections (CR-BSIs) within a catheter system.

Figure 4B:
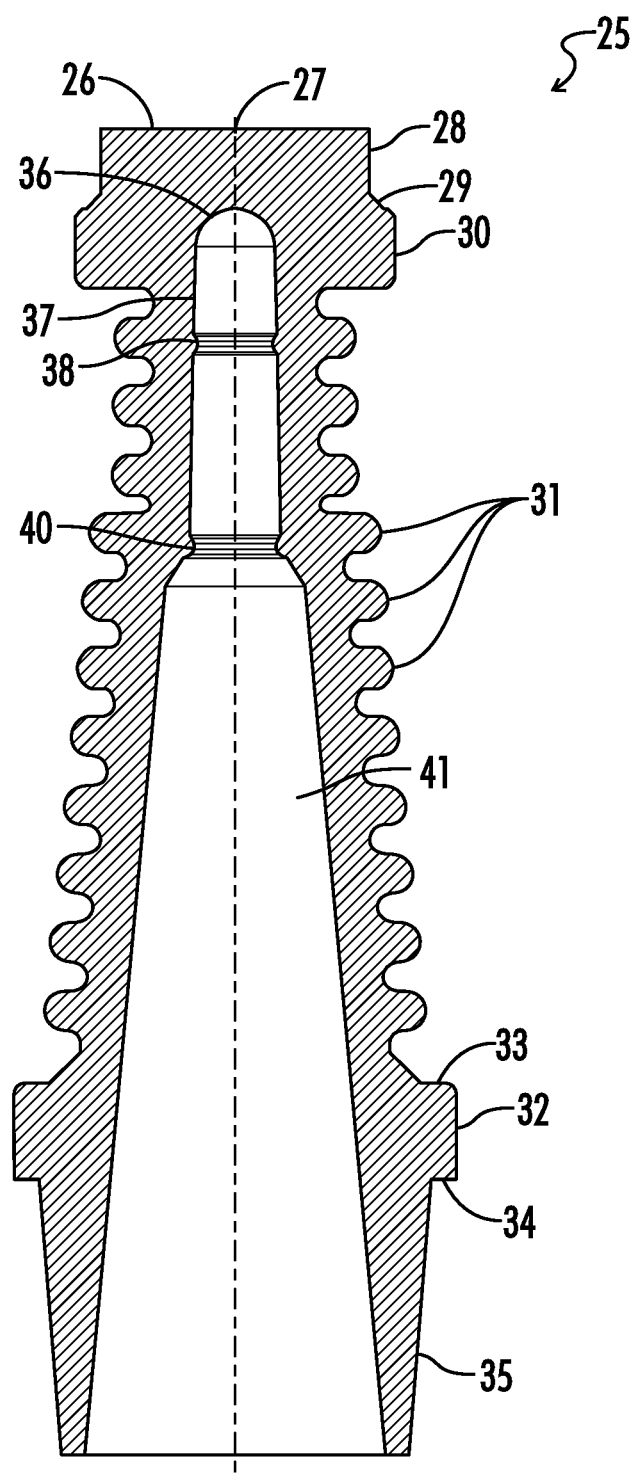
FIG. 4b is a cross-sectional view of the resilient microbial barrier of FIG. 4.

FIG. 4b is a full cross-sectional view of the resilient microbial barrier 25.

Figure 5:
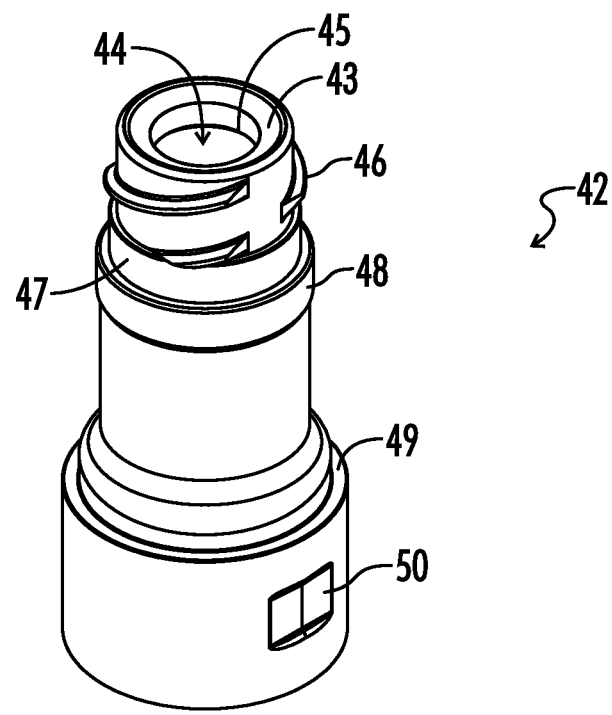
FIG. 5 is a perspective view of an embodiment of a second mating structure of the "standalone" needleless, intermittent, injection port assembly of FIG. 2.

FIG. 5 is a perspective view of the second mating structure 42 as shown in FIG. 2. A recessed, concave ring 43 can assist the healthcare provider when coupling the injection port 10 with a second connector such as with any fluid delivery or aspiration medical devices, i.e. standard syringe, IV administration sets, or blood collection systems. The recessed concave ring 43 guides the fluid delivery medical device male-luer tip towards the center of the resilient microbial barrier septum and prevents from slippage of the male-luer tip of the fluid delivery medical device during coupling to the injection port and which can help prevent potential contamination of the male-luer tip. A circular hole 44 is the entry point for the coupling of the second connector or any fluid delivery medical device. The circular hole 44 is defined by the tapered surface 45 of the second mating structure 42, the septum being received into the hole 44 when the microbial barrier is in the less compressed first position after assembly. The male-luer tapered surface 45 can form a compression fit with the upper sealing surface of the resilient microbial barrier as previously described herein. The male luer tapered surface 45 can be configured to produce an interference fit with male luer slip tip fluid delivery medical devices when the slip tip is inserted through the hole 44 and compresses the resilient microbial barrier. An exterior wall of the second mating structure 42 can also include a second set of threads 46 which can be configured to allow the injection port to be coupled to fluid delivery medical devices having male luer lock type connections. As such, the second mating structure 42 can allow the injection port to be coupled to medical devices having either a male luer slip tip configuration or a male luer lock configuration. In some embodiments, the second set of threads 46 can include standard ISO 594 engagement threads. Circular stabilizing ring 47 can help seat or position a threaded male-luer lock tip when the male luer lock tip is coupled to the second mating structure 42 of the injection port assembly. The circular stop ring 48 can provide a positive stop for a threaded male-luer lock tip after coupling to the second mating structure 42 of the injection port assembly such that a distal end of a male-luer tip lumen in a male luer lock tip can be positioned slightly below the hollow cannula lateral side fluid pathway holes or slots, thereby opening up the fluid pathway for infusion of fluids or aspiration of blood. An external assembly ring 49 can be utilized to fit into the manufacturing machine circular hole fixtures for the final "press-fit" and snap-lock assembly process of the injection port. The external and recessed slots 50 on the proximal portion of the second mating structure 42 are for injection molding gate locations.

Figure 5A:
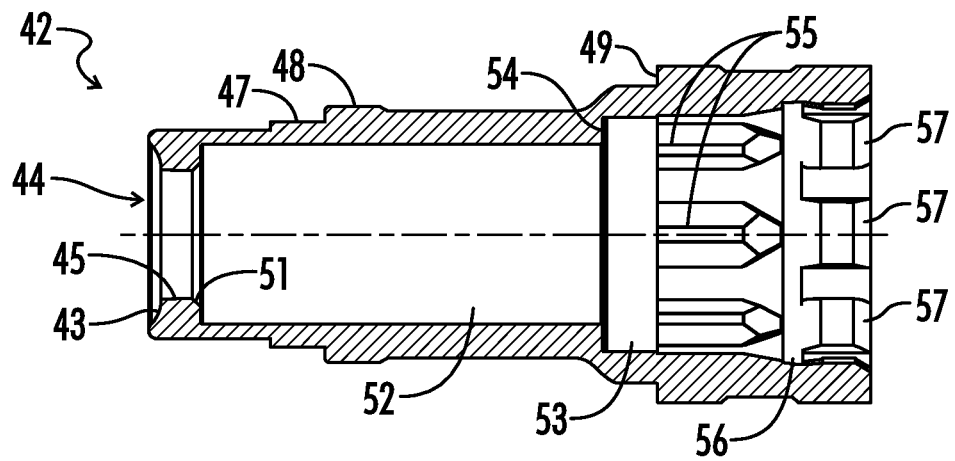
FIG. 5a is a cross-sectional view of the second mating structure of FIG. 5.

FIG. 5a is a cross-sectional view of the second mating structure 42 as shown in FIG. 5. This view reflects the recessed concave entry ring 43, the circular hole 44, and the male-luer tapered surface 45, the circular stabilizing ring 47, and the circular male-luer lock stop ring 48. The secondary sealing surface 51 can form a compression fit seal with the lower sealing surface of the resilient microbial barrier when the resilient microbial barrier is in the less compressed first position as previously described herein. The second mating structure 42 has an interior space 52. The resilient microbial barrier lower flange space 53 will be substantially filled by the resilient microbial barrier lower flange after assembly of the injection port. The lower sealing ring surface 54 of the second mating structure 42 can produce compression of resilient microbial barrier lower flange after assembly of the injection port 10. This compression design feature can produce seals on the resilient microbial barrier lower flange which can help prevent fluid and air leakage from the inside of the injection port during its life cycle of usage. The compression of the resilient microbial barrier lower flange can also help firmly secure the resilient microbial barrier within the injection port assembly. A second set of anti-rotation and self-guiding ratchets 55 are designed to couple with the first set of anti-rotation and self-guiding ratchets of the first mating structure. The self-guiding ratchets allow for full assembly automation of the body without the need for indexing the components. A snap-lock channel feature 56 can, by mechanically press-fitting, securely couple the second mating structure 42 to the first mating structure during assembly, the snap-lock channel 56 receiving the snap lock ring of the first mating structure to couple the first and second mating structures together. The stabilizing ring securement segments 57 are designed to securely snap-lock the first mating structure to the second mating structure 42 once the snap-lock ring is received into the snap-lock channel 56. The stabilizing ring securement segments 57 also stabilize the second mating structure 42 with the stabilizing ring shelf of the first mating structure.

FIG. 6 is a cross-sectional view of the present disclosure shown in FIG. 1. This view reflects the combination of features of the first mating structure 12, second mating structure 42, and the resilient microbial barrier 25. This cross-sectional assembly view of the assembly shown in FIG. 1 highlights the numerous compression-fit surfaces and seals previously discussed herein.

FIG. 6a is an enlarged cross-sectional view of the upper assembly of FIG. 6. This view shows the flat septum surface 26 and the razor slit 27 extending through the septum surface 26 through to the bullet nose mating surface 36. In some embodiments, the razor slit can be approximately 0.048" wide. Razor slit 27 in some embodiments can be performed as a post-injection molding operation. Numerous other means to form the slit of the present disclosure will be readily apparent to those of skill in the art, including the use of a knife-blade, hollow needle, blunt needle, or other suitable manufacturing method to form slit 27 in the resilient microbial barrier 25. This cross-sectional view shows the various compression-fit seals between the resilient microbial barrier 25 and the second mating structure 42, as well as the compression-fit seals between the resilient microbial barrier 25 and the cannula 19. The upper annular sealing ring 38 is positioned slightly above the lateral holes or slots 20 of the hollow cannula 19, and the lower annular sealing ring 40 is positioned slightly below the lateral holes or slots 20 of the hollow cannula 19, with the resilient microbial barrier in the less compressed first position.

FIG. 7 is an cross-sectional view of the injection port 10 shown in FIG. 6 having a second connector fluid delivery medical device 58, i.e. a standard male-luer slip syringe in a pre-coupling position to the "standalone" injection port assembly 10. Resilient microbial barrier 25 is shown in the less compressed first position before coupling of the second connector 58.

Figure 7A:
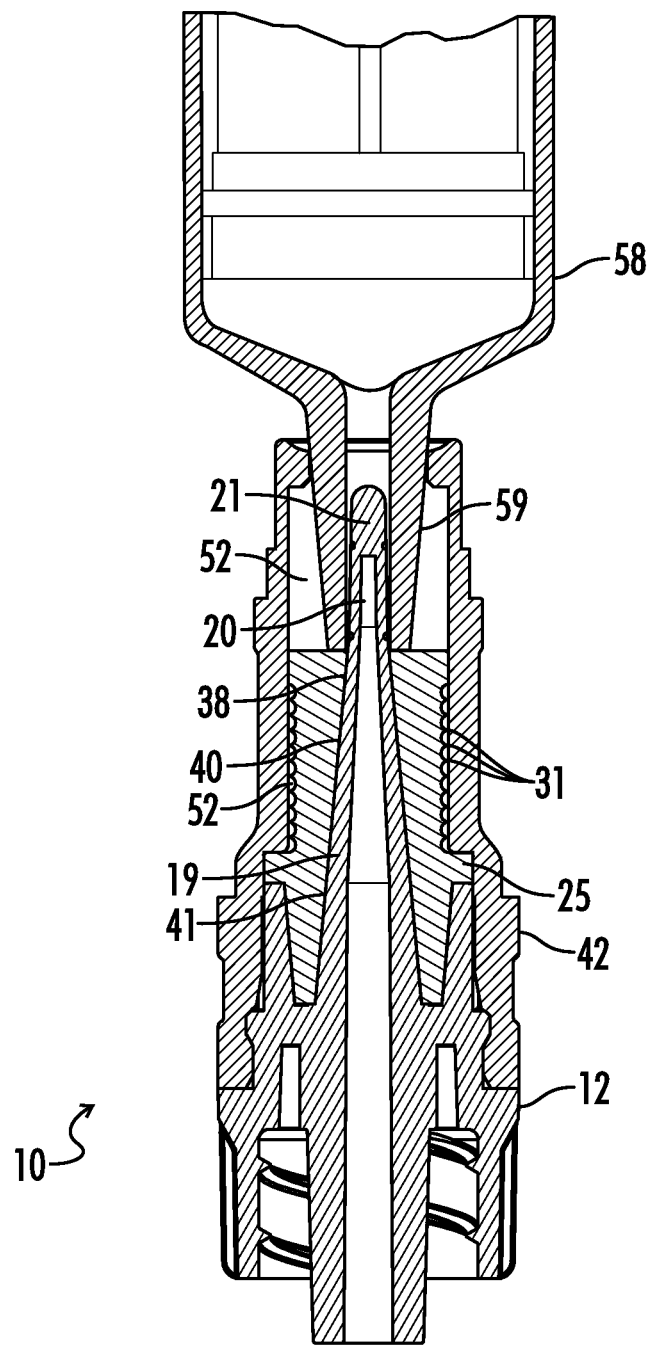
FIG. 7a is a cross-sectional view of a second connector male-luer slip syringe fully coupled to the "standalone" injection port assembly of FIG. 1 exposing hollow cannula side fluid pathway slots for infusion of fluids, or the aspiration of blood.

FIG. 7a is a cross-sectional view of the full assembly shown in FIG. 6a having a standard male-luer slip syringe 58 fully coupled to the "standalone" injection port assembly 10. The male-luer tip 59 of a second connector 58 fluid delivery medical device can further compress the resilient microbial barrier 25 during coupling of the second connector 58 to the injection port 10 to the more compressed second position, thereby exposing the distal portion of the hollow cannula 19 and the lateral side holes or slots 20, which can allow for infusion of fluids or the aspiration of blood from the patient. Once the infusion therapy or blood collection sample is completed, the second connector 58 will be uncoupled from the injection port assembly 10. The resilient microbial barrier 25, due to the series of accordion spring-like shaped flutes 31, will return to its original less compressed first position once again as shown in FIG. 7. During the coupling of a second connector 58 fluid delivery medical device to the injection port 10 and either the infusion of fluids through the hollow cannula 19 and vascular-access catheter fluid pathway or the aspiration of blood from the patient, the various sealing surfaces and features previously discussed can help prevent fluid or other liquids from leaking outside of the fluid pathway and into either the interior space 52 of the second mating structure 42, or the interior space 41 of the resilient microbial barrier 25.

FIG. 8 is a perspective view of the "standalone" needleless, intermittent, injection port assembly 10 of FIG. 1 coupling to a single-lumen, peripherally-inserted central catheter (PICC) 60. A PICC catheter is one of many central-venous catheter (CVC) options available to the physician or qualified healthcare provider based on the patient's needs and requirements. A PICC catheter 60 generally consists of a female-luer lumen 61 in which the "standalone" needleless, intermittent, injection port assembly 10 couples. A clear, soft, pliable tubing 64, a fluid flow slide or C-clamp 63a to close off the fluid pathway, a junction 63 where the tubing 64 and the catheter 62 are mated. PICC catheter lines 60 have grown in popularity over the past fifteen years, due to lower catheter-related bloodstream infection rates from more traditional central venous catheters, i.e. subclavian, femoral, tunneled chronic or internal jugular catheters. An additional advantage is the ability of trained nurse RN's to place a PICC catheter 60 versus the traditional interventional radiologist MD. Most central venous catheters (CVCs) will have one or more female-luer lumens 61 per catheter; a single-lumen, double-lumen, a triple-lumen catheter, or more. Each catheter female-luer lumen 61 is a separate fluid path through the central-venous catheter 62. Central-venous catheters (CVCs) also come in various French sizes, catheter lengths, catheter materials, and high-pressure capabilities options based on the patient requirements. The PICC catheter could stay in the patient for an extended period of time. Many patients will leave the hospital with their PICC catheter 60 in place and have a home infusion service care and maintain the catheter for occlusions and infection prevention. The needleless, intermittent, injection port 10 would be uncoupled from each of the catheter lumens, safely disposed of, and a new sterile injection port 10 would be re-coupled to the catheter approximately every 72 to 96 hours in an acute care setting, and up to 7 days in a home infusion setting.

FIG. 8a is a perspective view of the "standalone" needleless, intermittent, injection port assembly 10 coupling to a short-term, peripheral intravenous catheter 65 (PIV). The PIV catheter consists of a female-luer lumen 67 and a soft tube material catheter 66. Virtually every time a patient comes into the emergency room of an acute care hospital, a short-term, peripheral intravenous catheter (PIV) 65 will be inserted into the patient. Most non-critical patients, i.e. medical surgical floors, OB, etc. will use a PIV for infusion of fluids and antibiotics or blood collection for chemical analysis during the patients stay. Over 300 million PIV catheters are used annually in the United States alone. A needleless, intermittent injection port 10 is typically not coupled directly to the short-term PIV catheter 65. This is due to difficulty in coupling and uncoupling a fluid delivery medical device. A catheter-extension set is generally used with a short-term PIV catheter.

FIG. 8b is a perspective view of the "standalone" needleless, intermittent, injection port assembly 10 coupling to a single-lumen, catheter-extension set 68 which has been coupled to a short-term, peripheral intravenous catheter 65 (PIV). A catheter-extension set 68 generally consists of a female-luer lumen 69, in which the injection port 10 couples to, a soft, pliable, kink-resistant clear tubing 70, a slide or c-clamp 71 to impede fluid flow, and a male-luer lock or slip connector 72 which couples to the PIV catheter 65. Catheter-extension sets 68 also come in numerous configurations of tubing sizes and lengths, one or more female-luer lumens, and T-connectors based on the patient's needs and requirements.

FIG. 9 is a perspective view of another embodiment of a needleless, intermittent, injection port assembly 110 having a Y-site configuration. The Y-site injection port 110 consists of a first mating structure 112 having a y-injection site body, a second mating structure 42, and a resilient microbial barrier 25.

Figure 9C:
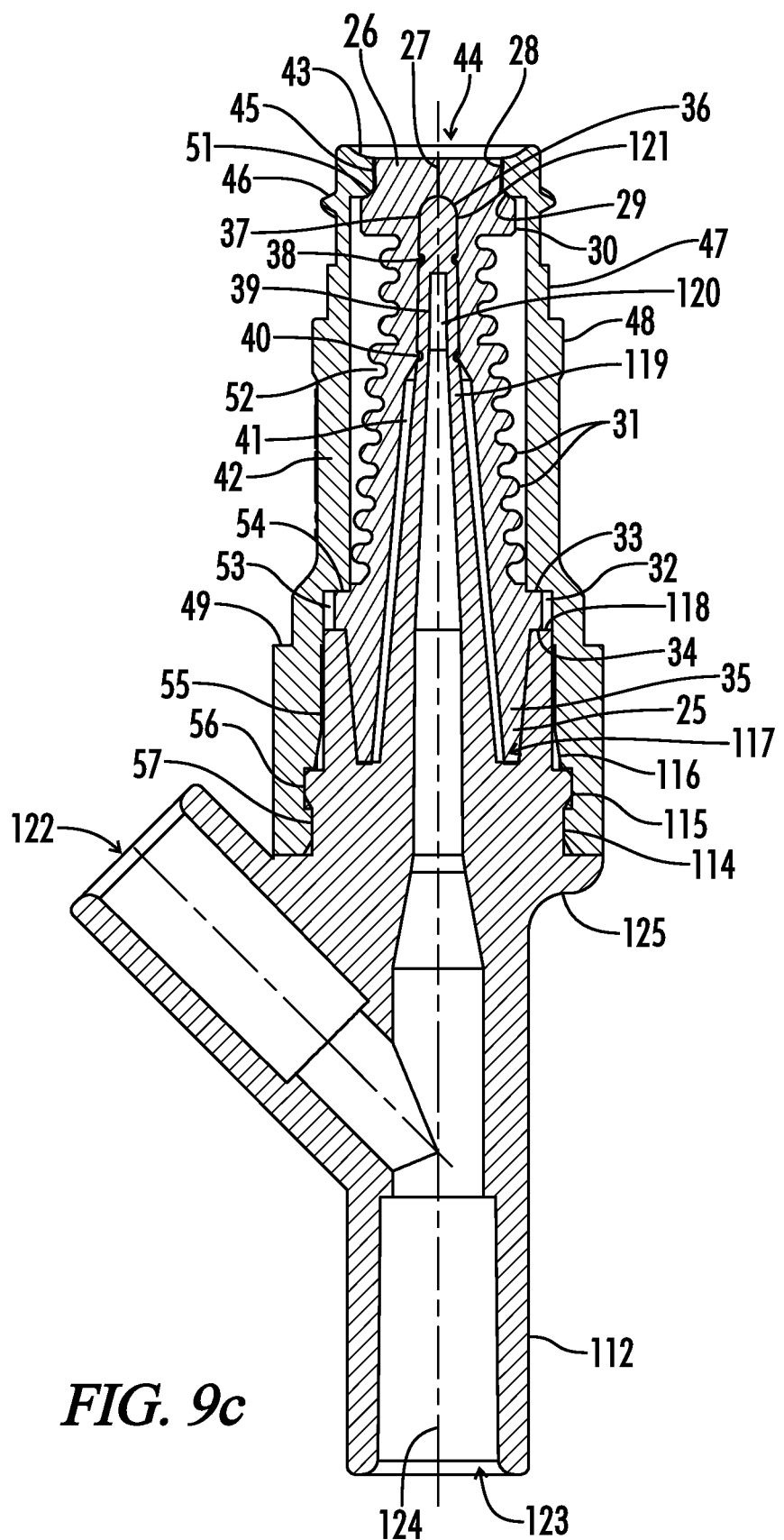
FIG. 9c is a cross-sectional view of the needleless, intermittent, Y-site injection port assembly of FIG. 9.

FIG. 9a is a perspective view of the first mating structure 112 of FIG. 9. The selected plastic material for the first mating structure 112 will be latex-free, non-DEHP, and Bisphenol-A free for improved patient safety. The stabilizing ring shelf segments 114 can help stabilize the second mating structure via the stabilizing ring securement segments 57, as shown in FIG. 9c and previously described herein. A snap-lock ring feature 115 can mechanically press-fit and help securely couple the first mating structure 112 to the second mating structure 42 during assembly, by coupling the snap-lock ring 115 to the second mating structure snap-lock ring channel 56. A series of anti-rotation and self-guiding ratchets 116 are designed to couple with the anti-rotation and self-guiding ratchets 55 of the second mating structure during assembly 10. The self-guiding ratchets allow for full assembly automation of the injection port 110 without the need for indexing the components. The sealing ring shelf 118 is the base for the resilient microbial barrier 25 lower flange ring 32 to sit on for a compression-fit sealing surface after assembly. A sealing well 117 is designed to couple with the resilient microbial barrier 25 lower compression-fit well ring 35 to form an additional fluid seal after assembly. A hollow fluid pathway cannula 119 is an integral part of the first mating structure 112. The fluid pathway 124 is straight-through and non-tortuous to help reduce any dead space within the fluid pathway, help provide a small priming volume, clinically-acceptable fluid flow rates, and to help minimize any blood fibrin or biofilm adhesion, development, and colonization. Along the upper portion of the hollow cannula 119 are lateral fluid pathway holes or slots 120. On the distal end of the hollow cannula 119 is a full radius bullet-nose 121 feature. This type of distal end is designed to increase the number of coupling and uncoupling events over the life-cycle of the Y-injection port 110. The first mating structure 112 having a Y-site configuration consists of two tubing fluid pathway channels 122 and 123. Soft, clear, pliable tubing will be permanently coupled to tubing channels 122 and 123 for a leak-proof fluid pathway 124.

FIG. 9b is a cross-sectional view of the Y-injection body 112 of FIG. 9a. The two IV tubing channels 122 and 123 are shown. The fluid pathways 124 within the Y-injection site body 112 reflect the typical fluid flow directions within the body 112. The external shell assembly ring 125 is utilized to fit into the manufacturing machine first mating structure 112 hole fixtures for the final "press-fit" and snap-lock assembly process of the Y-site injection port 110. The anti-rotation and self-guiding series of ratchets 116, sealing well ring 117 and sealing shelf 118. The hollow cannula 119 is shown to be an integral part of the first mating structure 112. The straight-through, non-tortuous, fluid pathway 124 is shown within the hollow cannula 119. The upper distal end lateral side fluid pathway holes or slots 120 of the hollow cannula 119 are shown along with the distal end bullet-nose feature 121.

FIG. 9c is cross-sectional view of the Y-injection site assembly 110 of FIG. 9. This view reflects the combination of features of the first mating structure 112, second mating structure 42 shown in FIG. 5, and the resilient microbial barrier 25 shown in FIG. 4. The cross-sectional view of the Y-site injection port 110 shown in FIG. 9 highlights the numerous compression-fit seals within the injection port 110 that help produce a substantially neutral displacement within the fluid pathway 24, which can help reduce intraluminal thrombotic catheter occlusions and catheter-related bloodstream infections.

FIG. 10 is perspective view of the Y-injection site assembly 110 incorporated into a gravity-fed, intravenous administration set. A typical gravity-fed, intravenous administration set consists of a solution bag or bottle 126, a drip chamber 127, soft, pliable tubing 128, one or more slide clamps, c-clamps, or roller clamps 129 to impede or close off fluid flow, one or more Y-site injection ports 110, and a male-luer lock or slip connector 130 that can be coupled to a standalone injection port 10.

Thus, although there have been described particular embodiments of the present invention of a new and useful Needleless, Intermittent, Neutral Displacement IV Injection Port it is not intended that such references be construed as limitations upon the scope of this invention except as set forth in the following claim.

What is claimed is:

1. An injection port assembly comprising:
    a body having a first mating structure configured to mate with a first connector and a second mating structure coupled to the first mating structure and configured to mate with a second connector;
    a resilient barrier substantially contained within the body and compressible from a less compressed first position configured to block fluid flow between the first connector and the second connector to a more compressed second position configured to permit fluid flow between the first connector and the second connector, the resilient barrier including an inner wall;
    the second mating structure includes a distal body end portion having a distal end flange extending laterally inward, the distal end flange having defined therein a first inner tapered body surface and a second inner tapered body surface positioned proximally of the first inner tapered body surface;
    a hollow cannula coupled to the first mating structure and disposed within the resilient barrier, the hollow cannula having a distal end configured to extend through the resilient barrier when the resilient barrier is in the more compressed second position, the distal end having one or more lateral fluid pathway slots;
    a first annular sealing ring located on the inner wall of the resilient barrier, the first annular sealing ring positioned distally from the one or more lateral fluid pathway slots when the resilient barrier is in the less compressed first position; and
    a second annular sealing ring located on the inner wall of the resilient barrier, the second annular sealing ring positioned proximally from the one or more lateral fluid pathway slots when the resilient barrier is in the less compressed first position, the inner wall extending linearly between the first and second annular sealing rings;
    the resilient barrier includes a sealing flange configured to be compressed between the first and second mating structures when the second mating structure is coupled to the first mating structure;
    wherein when the resilient barrier is in the less compressed first position, the entire first inner tapered body surface of the second mating structure is in sealing engagement with the resilient barrier; and
    the hollow cannula further comprising a first annular groove positioned distally from the one or more lateral fluid pathway slots and a second annular groove positioned proximally from the one or more lateral fluid pathway slots for seating the first and second annular sealing rings when the resilient barrier is in the less compressed first position.

2. The assembly of claim 1, wherein the first and second annular sealing rings are configured to continuously engage the hollow cannula as the resilient barrier is compressed from the first position to the second position, and as the resilient barrier returns from the second position to the first position.

3. The assembly of claim 1, wherein:
    the distal end of the hollow cannula has an outer diameter, the first annular sealing ring has a first uncompressed inner diameter, and the second annular sealing ring has a second uncompressed inner diameter;
    the ratio of the outer diameter to the first uncompressed inner diameter is greater than 1; and
    the ratio of the outer diameter to the second uncompressed inner diameter is greater than 1.

4. The assembly of claim 1, wherein: the resilient barrier further includes a septum; and
    the septum is received through the opening in the second mating structure when the resilient barrier is in the first position, the first inner tapered surface producing an inward compression force on the septum that produces a first seal between the resilient barrier and the first inner tapered surface.

5. The assembly of claim 4, wherein:
    the resilient barrier further includes a second sealing surface; and
    the second inner tapered body surface compressing the second sealing surface of the resilient barrier when the resilient barrier is in the less compressed first position.

6. The assembly of claim 1, wherein the first mating structure and the hollow cannula are integrally formed.

7. The assembly of claim 1, wherein the first mating structure includes a Y-site configuration.

8. The assembly of claim 1, wherein when the resilient barrier is in the first position, the first annular sealing ring forms a first seal distally from the one or more lateral fluid pathway slots in the distal end of the hollow cannula, and the second annular sealing ring forms a second seal proximally from the one or more lateral fluid pathway slots in the distal end of the hollow cannula.

9. The assembly of claim 1, further comprising:
    a first locking portion disposed on the first mating structure;
    a second locking portion disposed on the second mating structure, the second locking portion corresponding to the first locking portion,
    wherein the first and second locking portions are configured to lock together to couple the second mating structure to the first mating structure.

* * * * *